United States Patent
Shin et al.

(10) Patent No.: US 8,192,549 B2
(45) Date of Patent: Jun. 5, 2012

(54) APPARATUS AND METHOD FOR HYDROLYSIS OF CELLULOSIC MATERIAL IN A TWO-STEP PROCESS

(75) Inventors: Namhee Shin, Clifton Park, NY (US); C. Bertil Stromberg, Diamond Point, NY (US); Thomas Pschorn, Lennoxville (CA)

(73) Assignee: Andritz Inc., Glens Falls, NY (US)

( * ) Notice: Subject to any disclaimer, the term of this patent is extended or adjusted under 35 U.S.C. 154(b) by 209 days.

(21) Appl. No.: 12/478,335

(22) Filed: Jun. 4, 2009

(65) Prior Publication Data

US 2009/0318679 A1    Dec. 24, 2009

Related U.S. Application Data

(60) Provisional application No. 61/060,292, filed on Jun. 10, 2008.

(51) Int. Cl.
*C13B 20/00* (2011.01)
*C13B 10/14* (2011.01)
*C13B 35/06* (2011.01)

(52) U.S. Cl. ............... 127/46.1; 127/9; 127/44

(58) Field of Classification Search .............. None
See application file for complete search history.

(56) References Cited

U.S. PATENT DOCUMENTS

| | | | |
|---|---|---|---|
| 3,380,883 A | 4/1964 | Richter et al. | |
| 3,413,189 A | 11/1968 | Backlund | |
| 2008/0295981 A1 | 12/2008 | Shin et al. | |
| 2008/0302492 A1 | 12/2008 | Shin et al. | |

FOREIGN PATENT DOCUMENTS

WO    2007/051269    5/2007

OTHER PUBLICATIONS

U.S. Appl. No. 12/478,353 of Namhee Shin et al., filed Jun. 4, 2009.

*Primary Examiner* — Emily Le
*Assistant Examiner* — Sarah A Slifka
(74) *Attorney, Agent, or Firm* — Nixon & Vanderhye P.C.

(57) ABSTRACT

A system and method for extracting pentose from a slurry of cellulosic material comprising cellulose, water, and optionally acid in a two-stage process.

3 Claims, 1 Drawing Sheet

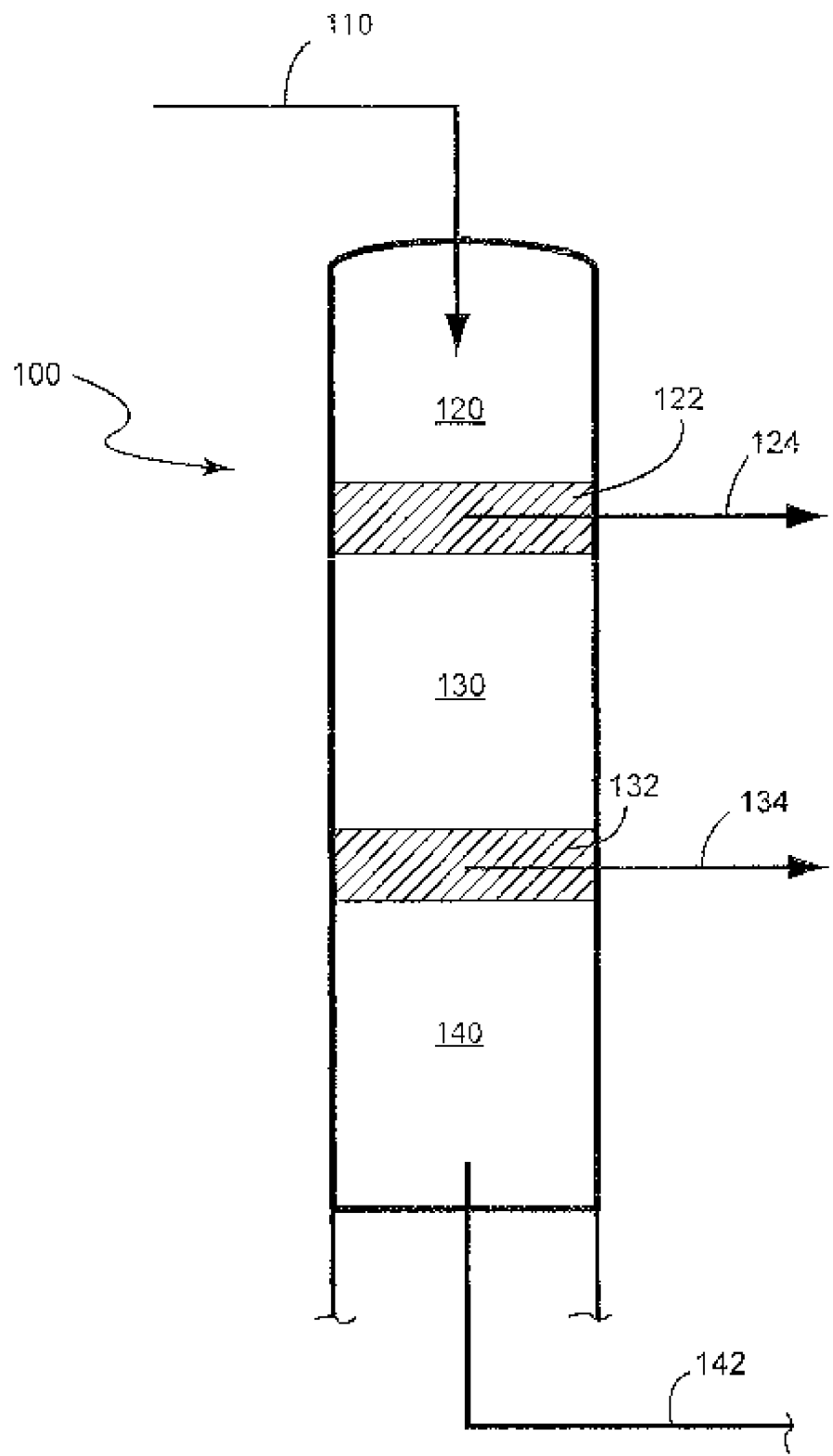

APPARATUS AND METHOD FOR HYDROLYSIS OF CELLULOSIC MATERIAL IN A TWO-STEP PROCESS

RELATED APPLICATION

This application claims the benefit of priority to U.S. Provisional Patent Application No. 61/060,292 filed Jun. 10, 2008, the entirety of which is incorporated by reference herein.

BACKGROUND OF THE INVENTION

This invention relates to a method and an apparatus for hydrolysis treatment of cellulosic fiber material.

In conventional systems, wood chips (or other cellulosic or fiber material) can undergo hydrolysis in a single vessel prior to treatment or cooking in a digester, such as described in U.S. Pat. Nos. 3,380,883 and 3,413,189. In such systems, hydrolysis occurs under acidic conditions in the slurry of wood chips, e.g., cellulosic material, passing through a top section of the vessel with the continued treatment of cooking in lower sections of the vessel followed by washing in the bottom of the vessel. In the upper region of the vessel, hydrolysate, e.g., sugars such as $C_5$ (pentose) and hemicellulose, is extracted from wood chips and the hydrolysate is recovered.

Hydrolysis occurs throughout the upper region of the vessel by the introduction of steam, acid and/or water in a concurrent flow in the upper region. In the lower region of the vessel, the cellulosic material is cooked and wash and is subsequently discharged as pulp from the vessel.

It is generally believed that performing the hydrolysis at a high temperature may produce the greatest volume of desired sugars. But high temperature treatment of wood or other cellulosic material may cause operational problems for the reaction vessel. For example, the treatment (hydrolysis) of cellulosic material at temperatures over 170° C. may cause the lignin to dissolve and may lead to an accumulation of the lignin in the vessel, especially on the internal surfaces. To avoid this lignin dissolving and accumulation in the vessel, the vessels may be operated at lower temperatures and for longer time. This may require a larger vessel resulting in a higher capital investment.

Other methods of hydrolyzing cellulosic material are described in U.S. application Ser. No. 12/114,856 (U.S. Pat. App. Pub. No. 2008/0302492) and Ser. No. 12/114,881 (U.S. Pat. App. Pub. No. 2008/0295981).

In certain aspects, the present invention may relate to hydrolyzing cellulosic material while minimizing any undesirable effects with respect to lignin (e.g., accumulation within the reaction vessel).

BRIEF DESCRIPTION OF THE INVENTION

The purpose of the invention is to dissolve the vast majority of hemicellulose and the majority of the cellulose present in the feed material, thereby chemically disintegrating the structure of the lignin cellulosic feed stock particles, such that the material will form a soup-like material.

In an aspect, an embodiment generally relates to an apparatus for extracting pentose from a slurry of cellulosic material comprising cellulose, water, and optionally acid, the apparatus comprising (i) an inlet adapted to receive the slurry at a top of a vessel, (ii) a first stage in which the slurry is exposed to a temperature between 130° C. and 190° C. for a period of time ranging between 10 minutes and 120 minutes, (iii) a first extraction screen and line that remove liquid containing $C_5$ sugars (pentose) from the slurry may be present, (iv) a second stage in which the slurry is exposed to a temperature between 100° C. and 170° C. for a period of time ranging between 30 minutes and 120 minutes, (v) a second extraction screen and line that remove liquid containing $C_5$ sugars (pentose) and hemicellulose (such as $C_6$ sugars) from the slurry, and (vi) an outlet adapted to remove the slurry from a bottom of a vessel. A single vessel may contain the first and second stages, or these stages may be split across multiple vessels.

In an aspect, an embodiment generally relates to a method for extracting $C_5$ sugars (pentose) from a slurry of cellulosic material comprising cellulose, water, and optionally acid, the method comprising the steps of: feeding the slurry of cellulosic material comprising cellulose, water, and optionally acid to a first stage via an inlet at a top of a vessel; exposing the slurry in the first stage to a temperature between 130° C. and 190° C. for a period of time ranging between 10 minutes and 120 minutes; optionally if desired, extracting liquid comprising $C_5$ sugars (pentose) from the slurry in the first stage; feeding the slurry to a second stage; exposing the slurry in the second stage to a temperature between 100° C. and 170° C. for a period of time ranging between 30 minutes and 120 minutes; extracting liquid comprising $C_5$ sugars (pentose) and hemicellulose (including $C_6$ sugars) from the slurry in the second stage; and extracting the slurry via an outlet at the bottom of a vessel.

BRIEF DESCRIPTION OF THE DRAWINGS

FIG. 1 is an illustrative schematic diagram of a reactor vessel in accordance with an embodiment.

DETAILED DESCRIPTION OF THE INVENTION

In certain aspects, the present invention generally relates to a method and apparatus to dissolve $C_5$ sugars from cellulosic material. Preferably, the traditional Kraft cooking process is not used to produce dissolved $C_5$ sugars. $C_5$ sugars include, for example, xylose, arabinose and other pentoses. Hemicellulose includes $C_6$ sugars including, for example, glucose, mannose, other hexoses, etc.

In certain aspects, the cellulosic material may be partially or fully hydrolyzed in a two-step process. Cellulosic material may be fed to the top of a vessel (e.g., a cylindrical reaction vessel) in a slurry. The cellulosic slurry may be fed using a pump, hydrostatic pressure, or any other method of delivering the slurry to a top of a vessel.

The pH of the slurry containing cellulosic material may be between 0 and 7. In certain embodiments, the slurry may contain water or a mixture of water and acid to achieve the desired pH. In certain embodiments, upon entering the vessel, the slurry of material is heated to a temperature of between 130° C. and 190° C. (and all subranges therebetween) and has a liquid to wood ratio of between 1 to 1 and 1 to 10 (and all subranges therebetween).

In certain embodiments, there may be a hydrolysis stage with a short or very short duration or residence time where the temperature is over 170° C. This short time period may facilitate dissolving $C_5$ sugars while inhibiting dissolving lignin. In such a hydrolysis stage, it is believed that the linkage or bond between the $C_5$ sugars, the hemicellulose and the lignin is broken (thus yielding the $C_5$ sugars). It is believed that the lignin does not dissolve because the location of the lignin in the cellulosic material may require a longer treatment or exposure time to dissolve the lignin.

According to certain embodiments, the cellulosic material is held in a first stage of hydrolysis for a short time and at a high temperature. In certain embodiments, the time period may last between 10 and 120 minutes (and all subranges therebetween). In certain embodiments, the temperature may be between 130 and 190° C. (and all subranges therebetween) and preferably above 170° C. if acid is not added to the slurry. If acid is added to the slurry, the temperature in this first stage may be lowered, but would be above 130° C. In this stage, it is believed that the $C_5$ sugars are formed by breaking the linkage between the $C_5$ sugars, the hemicellulose and lignin. After the short, high temperature hydrolysis stage, liquid containing the $C_5$ sugars may be extracted and sent to further process units for processing, such as separation, purification, etc.

Following the first stage (and optional extraction if desired), the hot cellulosic material is cooled in a second stage. This cooling may require, but not necessitate, the addition of cool water. This cooler stage may facilitate the diffusion of the dissolved $C_5$ sugars from the hemicellulose, primarily leaving lignin and cellulose in the mass of cellulosic material. This second, cooler stage may occur for a period between 30 minutes and 2 hours (and all subranges therebetween) and at temperature between 100° C. and 170° C. (and all subranges therebetween), preferably at a temperature of 140° C. to 160° C. (and all subranges therebetween).

The second, cooler stage may be in the same vessel as the first stage or in a separate vessel. The cooling may be achieved in various methods, e.g., by injecting a cool liquid to reduce the temperature of the material and liquid in the vessel. Another exemplary method to cool the material in the vessel may relate to permitting flashing in the vessel, thereby reducing the temperature of the material and liquid in the vessel and producing steam that may be recovered and used elsewhere. It is also possible in a two-vessel system to employ indirect cooling using a circulation stream between the two vessels.

After the second, cooler stage, liquid containing hemicellulose and $C_5$ sugars is preferably removed from the cellulosic material mass and available for further processing. The hemicellulose in the liquid may include other dissolved material (e.g., $C_6$ sugars, such as hexose) as well. The resulting cellulosic material mass is available for further downstream processing (e.g., processing unrelated to removing a bulk amount of $C_5$ sugars).

FIG. 1 schematically illustrates an embodiment including a single vessel 100. A slurry of cellulosic material enters the top of vessel 100 via line 110. In preferred embodiments, the cellulosic slurry includes chips and/or pulp, water, and optionally acid. In other embodiments, further additives may be present in the cellulosic slurry, e.g., to facilitate the extraction of $C_5$ sugars from the cellulosic material.

After entering the vessel 100, the cellulosic slurry enters a first stage 120 where it is exposed to a temperature between 130° C. to 190° C. for a period of time between 10 to 120 minutes. After this stage, a liquid containing $C_5$ sugars (and possibly also other dissolved material, such as $C_6$ sugars like hexose) may be extracted via screen 122 and line 124. The hot cellulosic slurry then enters second stage 130, where it dwells for a period of time between 30 minutes and 2 hours at a temperature between 100° C. to 170° C. To achieve the cooler environment, it may be necessary to introduce cool water to this stage. After this second, cooler stage, a liquid containing $C_5$ sugars and hemicellulose (and possibly also other dissolved material, such as $C_6$ sugars) may be extracted via screen 132 and line 134. The slurry may optionally remain in the vessel 100 for further processing (e.g., entering a third stage 140) and/or be extracted via line 142.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for extracting $C_5$ sugars comprising pentose from a slurry of cellulosic material comprising cellulose and water, the method comprising the steps of:
    feeding the slurry of cellulosic material comprising cellulose and water to a first stage via an inlet at a top of a vessel, wherein the step of feeding the slurry of cellulosic material comprising cellulose and water to the first stage via the inlet at the top of the vessel does not comprise adding acid to the slurry;
    exposing the slurry in the first stage to a first temperature between 170° C. and 190° C. for a first period of time ranging between 10 minutes and 120 minutes;
    passing the slurry to a second stage; exposing the slurry in the second stage to a second temperature between 100° C. and 170° C. for a second period of time ranging between 30 minutes and 120 minutes;
    extracting liquid comprising $C_5$ sugars including pentose and $C_6$ sugars including hemicellulose from the slurry in the second stage; and
    extracting the slurry containing lignin via an outlet at the bottom of a vessel.

2. The method according to claim 1 further comprising the step of extracting liquid comprising $C_5$ sugars including pentose from the slurry in the first stage.

3. The method according to claim 1, wherein second temperature is between 140° C. and 160° C.

* * * * *